United States Patent [19]

Berg et al.

[11] Patent Number: 4,559,038
[45] Date of Patent: Dec. 17, 1985

[54] DRUG DELIVERY SYSTEM

[75] Inventors: Harvey F. Berg, Stacy; Lyle Peterson, Maple Grove; James E. Leslie, Mounds View, all of Minn.

[73] Assignee: Deltec Systems, Inc., St. Paul, Minn.

[21] Appl. No.: 663,050

[22] Filed: Oct. 19, 1984

[51] Int. Cl.$^4$ ............................................. A61M 5/00
[52] U.S. Cl. ................................... 604/153; 417/474; 417/476
[58] Field of Search ............................... 604/151–153, 604/34, 250, 131; 417/474, 476, 477, 478

[56] References Cited

U.S. PATENT DOCUMENTS

| | | | |
|---|---|---|---|
| 4,139,008 | 2/1979 | Wagner | 604/151 |
| 4,177,810 | 12/1979 | Gourlandt | 604/152 |
| 4,265,240 | 5/1981 | Jenkins | 604/151 |
| 4,273,260 | 6/1981 | Bush | 604/250 |
| 4,384,578 | 5/1983 | Winkler | 604/151 |
| 4,396,385 | 8/1983 | Kelly et al. | 604/152 |
| 4,411,651 | 10/1983 | Schulman | 604/151 |
| 4,456,223 | 6/1984 | Ebling | 604/34 |
| 4,460,358 | 7/1984 | Sommerville et al. | 604/34 |

*Primary Examiner*—D. E. Gantz
*Assistant Examiner*—Anthony McFarlane
*Attorney, Agent, or Firm*—Peterson, Wicks, Nemer, & Kamrath

[57] ABSTRACT

A system for delivering a drug to a patient according to the preferred embodiment of the present invention is shown as being of modular construction including a control module and a reservoir module. The reservoir module is removably secured to the control module by a removable hinge member at one end and a locking member at the other end. The reservoir module includes a pressure plate upon which a tube extending from a drug container bag to the patient is supported. The control module includes a pumping mechanism including a camshaft which reciprocates valves and an expulsor in the control module. The valves and expulsor engage and interact with the tube located on the pressure plate for forcing the drug from the drug container bag to the patient. In its most preferred form, the pressure plate includes standoffs which abut with the pump chassis for insuring proper spacing maintenance between the pressure plate of the reservoir module and the control module. The cam shaft is driven by a motor controlled by electronic controls included in the control module which may be preprogrammed to deliver a precise amount of drug over a specific period of time. The drug delivery system of the present invention may be removably secured to the patient allowing the patient to be ambulatory while being administered drugs.

21 Claims, 5 Drawing Figures

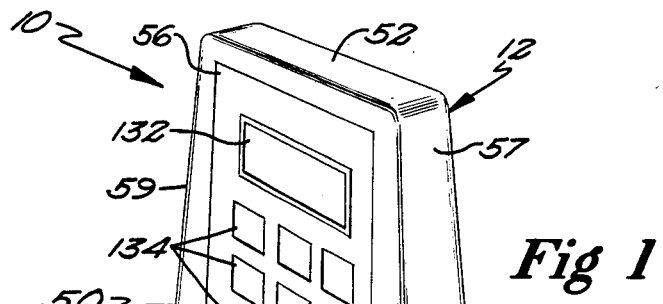
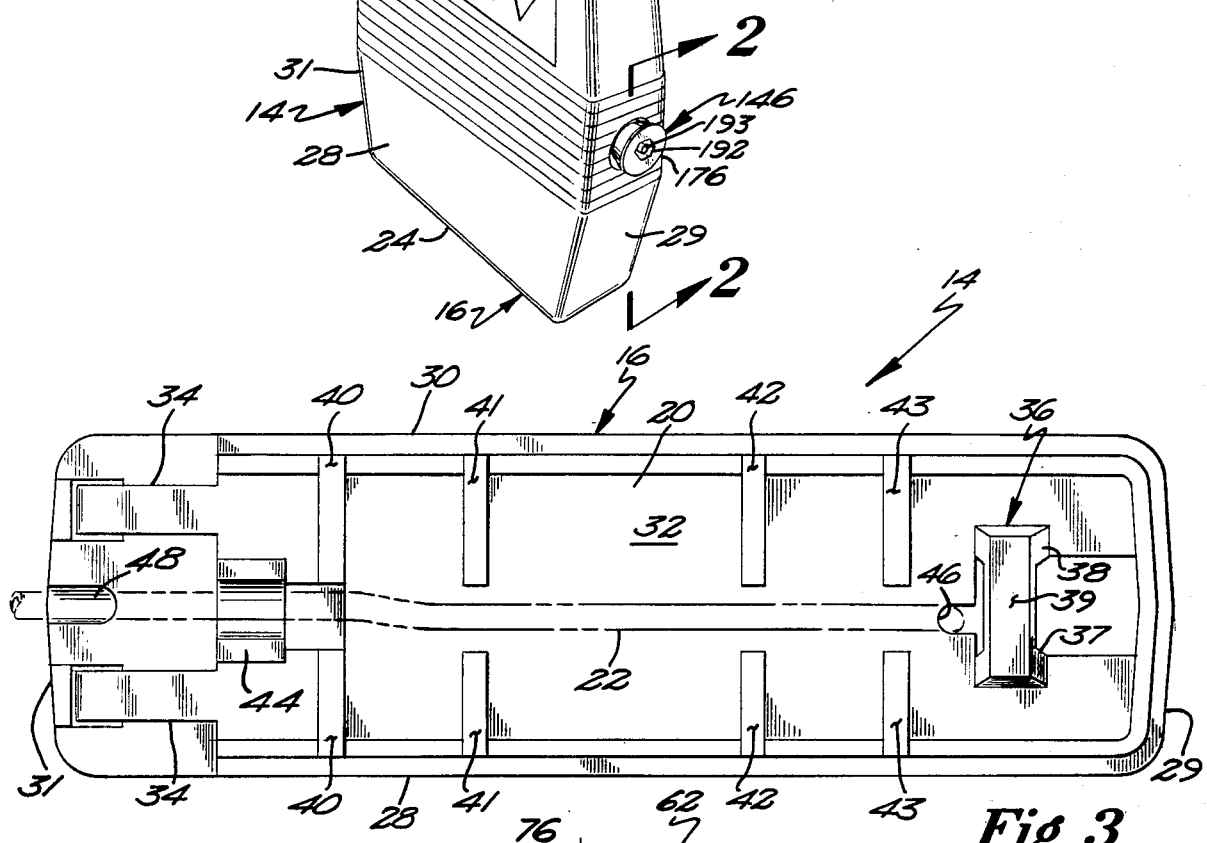
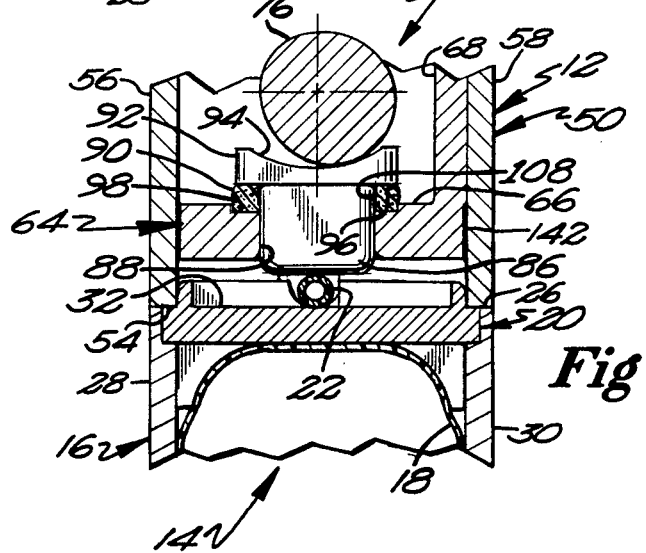

DRUG DELIVERY SYSTEM

BACKGROUND

The present invention relates generally to the delivery of drugs to patients, particularly to systems for providing drug delivery, and specifically, to systems for providing continuous drug delivery.

Certain drugs rarely achieve their maximum therapeutic action through conventional injection techniques. The therapeutic activity of such a drug is improved considerably when it is delivered at controlled rates to maintain optimum drug concentration for a specific period. In a typical drug injection, a greater dosage than necessary must be administered to keep the drug concentration within the effective therapeutic margin for the minimum period needed for treatment. With controlled drug infusion, the drug can be given at a precise rate that will keep the drug serum concentration within the therapeutic margin and out of the toxic range. Continuous drug delivery is assuming an ever increasing role in the treatment of acute and chronic illnesses. Many drugs reach their full potential only through precise delivery over an extended period of time.

Continuous intravenous infusion has been the only conventional method of administering drugs at constant controllable rates for prolonged periods. Conventional equipment requires the patient to be hospitalized and attended by medical professionals frequently. These requirements make the system somewhat impractical and expensive for a non-critical patient who could be treated outside the hospital.

Thus a need has arisen for a system for providing continuous drug delivery to a patient at a controllable rate which does not require frequent medical attention and which allows the patient to be ambulatory.

SUMMARY

The present invention solves this and other needs by providing, in the preferred embodiment, a system for delivering a drug to a patient of a modular construction and including control and reservoir modules. The reservoir module is removably secured to the control module. The reservoir module includes a drug container and a member which allows passage of the drug from the container to the patient. The control module includes a member for forcing the passage of the drug from the container to the patient. When the reservoir module is secured to the control module, the drug forcing member of the control module interacts with the drug passage member of the reservoir module for purposes of delivering a drug stored in the drug container to the patient at desired rates. In its most preferred form, the drug delivery system of the present invention can be secured to the patient and allows the patient to be ambulatory.

It is thus an object of the present invention to provide a novel system for providing drug delivery.

It is further an object of the present invention to provide such a novel drug delivery system which provides drug delivery at a controllable rate.

It is further an object of the present invention to provide such a novel drug delivery system which does not require frequent medical attention.

It is further an object of the present invention to provide such a novel drug delivery system having a modular construction.

It is further an object of the present invention to provide such a novel drug delivery system which is more user friendly than prior drug delivery systems.

It is further an object of the present invention to provide such a novel drug delivery system which allows the use of disposable reservoir modules.

It is further an object of the present invention to provide such a novel drug delivery system including an efficient, accurate, and inexpensive pumping mechanism.

It is further an object of the present invention to provide such a novel drug delivery system wherein the pumping chamber upon which the pumping mechanism interacts is disposable with each replacement drug container.

It is further an object of the present invention to provide such a novel drug delivery system which allows the physician to preprogram the system to deliver a precise amount of drug over a specific period of time.

It is further an object of the present invention to provide such a novel drug delivery system which may be worn externally by the patient.

It is further an object of the present invention to provide such a novel drug delivery system which allows certain intravenous therapies to be given outside the hospital.

It is further an object of the present invention to provide such a novel drug delivery system which may reduce health care costs.

It is further an object of the present invention to provide such a novel drug delivery system which will give the patient a more normal lifestyle.

These and further objects and advantages of the present invention will become clearer in light of the following detailed description of an illustrative embodiment of this invention described in connection with the drawings.

DESCRIPTION OF THE DRAWINGS

The illustrative embodiment may best be described by reference to the accompanying drawings where:

FIG. 1 shows a perspective view of an ambulatory drug delivery system constructed according to the preferred embodiment of the present invention.

FIG. 3 shows a top view of the ambulatory drug delivery system of FIG. 1 according to view line 3—3 of FIG. 2.

FIG. 4 shows a partial, cross sectional view of the ambulatory drug delivery system of FIG. 1 according to section line 4—4 of FIG. 2.

Figure 2:
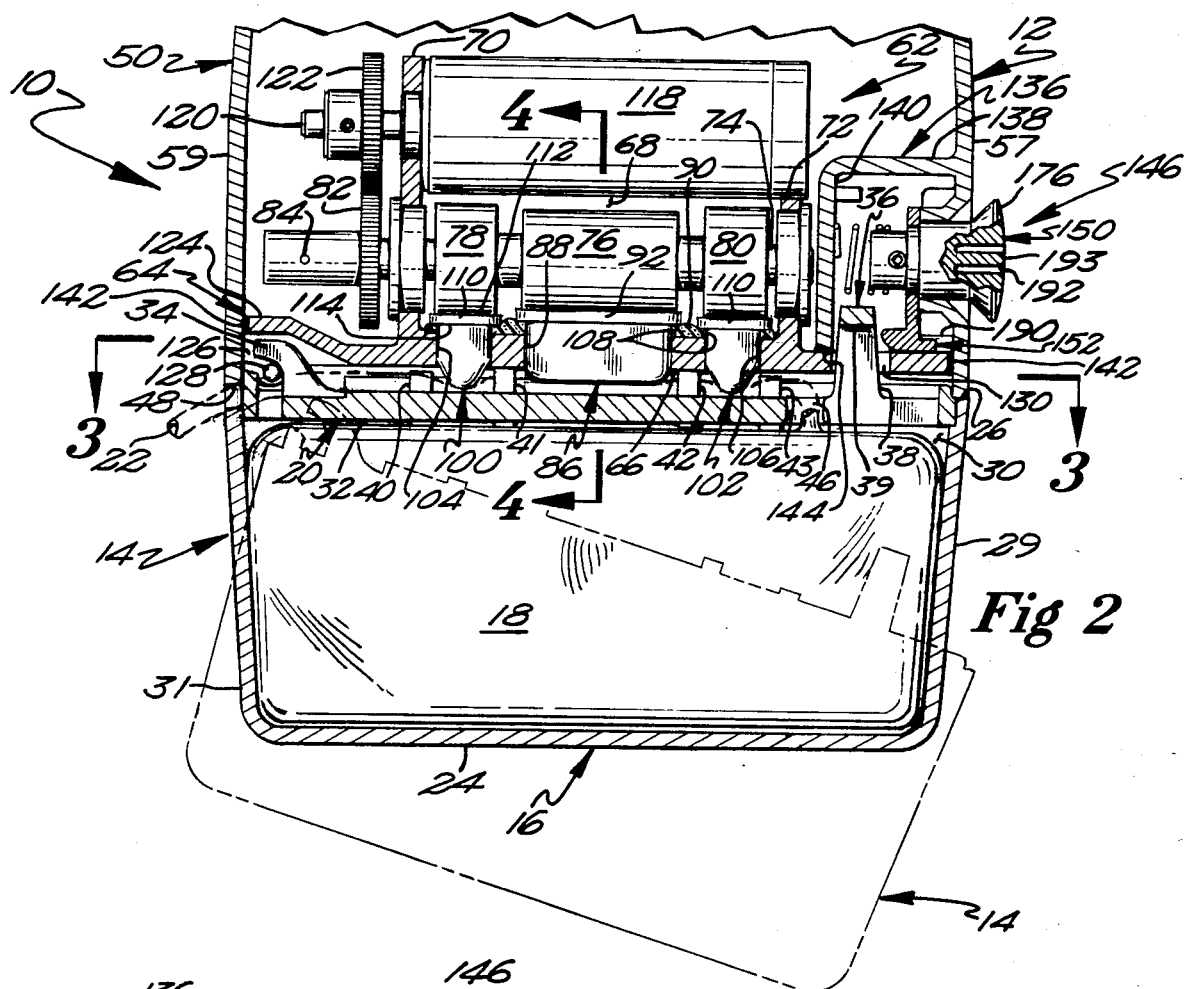
FIG. 2 shows a partial, cross sectional view of the ambulatory drug delivery system of FIG. 1 according to section line 2—2 of FIG. 1, with the reservoir module shown in its separated position in phantom.
Figure 5:
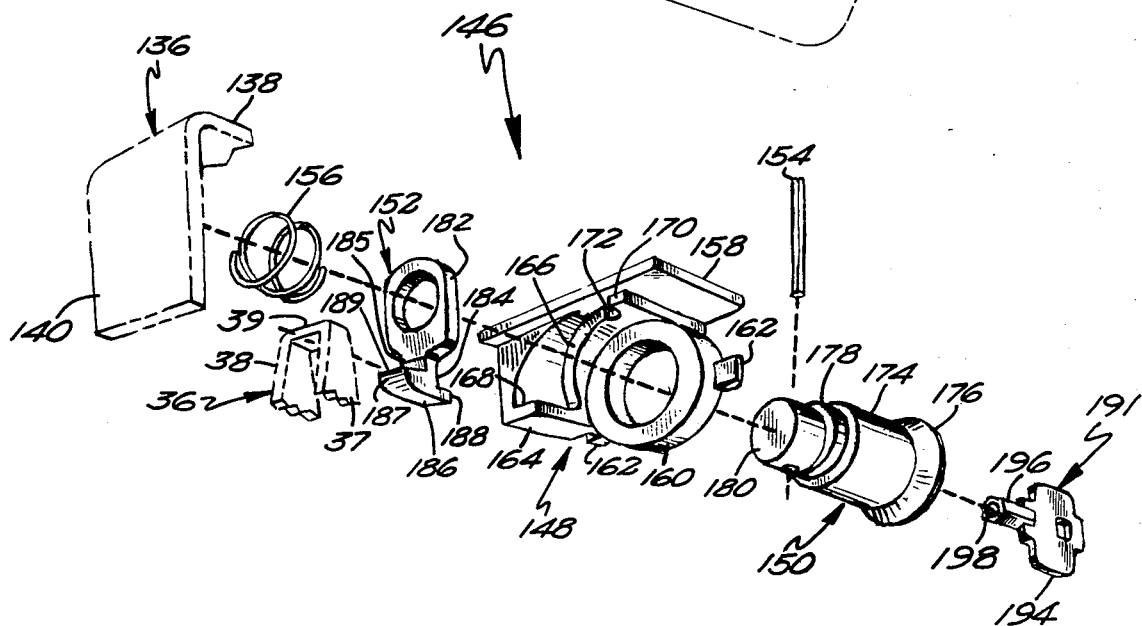
FIG. 5 shows an exploded perspective view of the locking mechanism of the ambulatory drug delivery system of FIG. 1.

All figures are drawn for ease of explanation of the basic teachings of the present invention only; the extensions of the Figures with respect to number, position, relationship, and dimensions of the parts to form the preferred embodiment will be explained or will be within the skill of the art after the following teachings of the present invention have been read and understood.

Further, the exact dimensions and dimensional proportions to conform to specific force, weight, strength, and similar requirements will likewise be within the skill of the art after the following teachings of the present invention have been read and understood.

Where used in the various figures of the drawings, the same numerals designate the same or similar parts. Furthermore, when the terms "top", "bottom", "first", "second", "inside", "outside", and similar terms are used herein, it should be understood that these terms have reference only to the structure shown in the drawings as it would appear to a person viewing the drawings and are utilized only to facilitate describing the invention.

DESCRIPTION

A system for providing ambulatory drug delivery is shown in the drawings according to the preferred embodiment of the present invention and generally designated 10. System 10 is particularly adapted for securement to a patient such as by a belt allowing the patient to be ambulatory while having continuous infusion of a drug at the desired rate. System 10 in its most general preferred form includes a control module 12 and a reservoir module 14.

Reservoir module 14 in its most preferred form includes a reservoir casing 16, a medicament container 18 shown in its most preferred form as a heat sealed vinyl bag, and a pressure plate 20. Bag 18 further includes a member 22 for providing communication between bag 18 and an infusion catheter of the patient and is shown in its most preferred form as an elastomeric tube. In its most preferred form, casing 16 is tub shaped and includes a generally closed bottom 24, a generally open top 26, and generally closed sidewalls 28–31.

Pressure plate 20 in the preferred embodiment shown generally includes a flat portion 32 having a shape complementary to and for receipt in open top 26 of casing 16. Pressure plate 20 in its most preferred form includes hooked portions 34 which upstand from flat portion 32 at a first end thereof. In its preferred form shown, pressure plate 20 further includes an inverted U-shaped member 36 upstanding from flat portion 32 at its end opposite to hooked portions 34. Specifically, member 36 includes first and second legs 37 and 38 having their first ends connected to flat portion 32 and their second ends connected to a central portion 39 which is generally parallel to flat portion 32. Pressure plate 20 in the preferred embodiment shown further includes standoffs 40–43 upstanding from the top surface of flat portion 32 to a height for purposes set forth hereinafter. Standoffs 40–43 generally include first and second portions which extend between the sides of flat portion 32 and which are separated by a distance generally equal to the diameter of tube 22. Pressure plate 20 in the preferred embodiment shown further includes a trough portion 44 located between standoff 40 and the first end of plate 20 including hooked portions 34 having a size and shape complementary to and for receiving tube 22. In the preferred embodiment, tube 22 extends through an opening 46 formed in flat portion 32 adjacent member 36, extends between the first and second portions of standoffs 40–43, extends through trough portion 44, and through a removed portion 48 formed in the end of flat portion 32 adjacent hooked portions 34. In its most preferred form, tube 22 lies on flat portion 32 of pressure plate 20 generally midway between and parallel to the sides of flat portion 32. Tube 22 in the preferred embodiment of the present invention is secured to pressure plate 20 by a solvent bond located between tube 22 and trough portion 44 and is anchored by its other end to pressure plate 20 and reservoir module 14 by its securement to bag 18 captured between pressure plate 20 and casing 16 and its passage through opening 46 of pressure plate 20.

Control module 12 in its most preferred form includes a casing 50 shown in its most preferred form formed of first and second halves and includes a generally closed top 52, a generally open bottom 54, and generally closed sidewalls 56–59.

Control module 12 further includes a member 62 interacting with tube 22 for forcing liquid from bag 18 through tube 22 and for preventing free flow of liquid through tube 22 either to or from bag 18. Member 62 is shown in its most preferred form as a pumping mechanism. Pumping mechanism 62 includes a chassis 64 including a first flat portion 66 and a second flat portion 68 generally at right angles to each other. In the preferred form, flat portion 68 has a shorter length than portion 66 and the ends of flat portion 68 are both spaced from the respective ends of portion 66. Chassis 64 further includes braces 70 and 72 which extend between portion 66 and the ends of portion 68 and which are spaced from each other and the ends of portion 66.

Pumping mechanism 62 further includes in its most preferred form a camshaft 74 rotatably mounted between braces 70 and 72 and having a first cam portion 76 located between second and third cam portions 78 and 80 on shaft 74. Shaft 74 extends through brace 70 and further includes a driven gear 82 and an optical switch indicator 84 shown in its most preferred form as a flag located between the end of portion 66 and brace 70.

In the preferred embodiment, pumping mechanism 62 further includes an expulsor 86 which is slideably mounted in an aperture 88 formed in portion 66. Expulsor 86 includes a head portion 92 including an arcuate portion 94 for engaging with cam portion 76 and an abutment surface 96 which prevents expulsor 86 from passing through aperture 88 of chassis 64.

In the preferred embodiment, pumping mechanism 62 further includes first and second valves 100 and 102 which are slideably mounted in apertures 104 and 106 formed in portion 66 of chassis 64, respectively. Valves 100 and 102 each include a head portion 110 having an arcuate portion 112 for engaging with cam portions 78 and 80 and having an abutment surface 114 which prevents valves 100 and 102 from passing through apertures 104 and 106 of chassis 64.

Provisions 90 are further provided for biasing expulsor 86 and valves 100 and 102 towards cam portions 76, 78, and 80 and for sealing expulsor 86 and valves 100 and 102 with flat portion 66 of chassis 64 of control module 12. In its most preferred form, provisions 90 is a closed cell foam gasket located in a cavity 98 formed in the top surface of flat portion 66 of chassis 64 and with which head portions 92 and 110 of expulsor 86 and valves 100 and 102 abut. Gasket 90 includes apertures 108 formed therein corresponding to apertures 88, 104, and 106 of chassis 64 and having a size and shape complementary to the receipt of expulsor 86 and valves 100 and 102. Gasket 90 has sufficient resiliency to bias expulsor 86 and valves 100 and 102 and has sufficient sealing ability to seal between chassis 64 and expulsor 86 and valves 100 and 102.

In its most preferred form, pumping mechanism 62 further includes a member 118 for driving camshaft 74 shown as a motor mounted between braces 70 and 72. Motor 118 includes a drive shaft 120 which extends through brace 70 having a drive gear 122 in gearing relation with gear 82 of camshaft 74. In its most preferred embodiment, motor 118 is a D.C. motor that rotates camshaft 74 through 360 degrees and then stops, with the number of rotations of shaft 74 controlling the volume of medicament being pumped from bag 18 of reservoir module 14.

In the preferred embodiment of the present invention shown, flat portion 66 of chassis 64 includes an upraised portion 124 located adjacent its first end having depending ears 126 extending therefrom. Hinge pins 128 are further provided extending between ears 126 generally parallel to flat portion 66. Hinge pins 128 are complementary to and for hingedly receiving hooked portions 34 of plate 20 of reservoir module 14. Flat portion 66 of chassis 64 further includes an aperture 130 located adjacent its opposite end complementary to and for receiving U-shaped member 36 of plate 20 of reservoir module 14.

Control module 12 further includes a source of power for motor 118, such as a battery, and suitable electronic controls for the operation of motor 118 for controlling the pumping of the liquid from bag 18 through tube 22. Included with the electronic controls, control module 12 may include a liquid crystal display (LCD) 132 and switches or keys, generally designated 134, for purposes of programming the electronic controls to start or stop the pump, to vary the rate of pumping, for priming the pump, to limit patient operation of the pump, and like functions. For example, programming modes of system 10 of the present invention may include: delivering drug concentrations of different rates; delivering a basal infusion at a set rate; allowing the patient the option of varying the basal rate up to the maximum rate allowed by the physician; delivering an incremental bolus dose at a set rate; allowing the patient the option of varying the incremental dose up to the maximum rate allowed by the physician; allowing the physician to set the minimum time between incremental doses; allowing the physician to limit the number of incremental doses per hour; and displaying the milligrams of medicament delivered, the number of incremental doses delivered, and the amount of volume of medicament remaining in the reservoir on the LCD 132. Thus, LCD 132 visually indicates various conditions of system 10 such as the rate of pumping, the volume of liquid remaining in bag 18, and like conditions. In its most preferred form, LCD 132 and keys 134 are located in sidewall 56 of casing 50 of control module 12. The electronic controls may further include a user interaction signal such as a buzzer or other audible alarm for purposes of indicating the condition of system 10 such as indicating the pressing of keys 134, a low battery, an empty reservoir, an error in programming the electronic controls, or like condition.

In other words, knowing factors such as the type and characteristics of the pumping mechanism and the type and concentration of medication, a manufacturer of a system according to the present invention would be in a position to program each system by modern electronics. That is, taking into account the above factors and other factors and contstraints set by modern medicine and the laws of physics, a manufacturer can program each system to receive such variables as: patient dosage; medicament concentration; the medication schedule; the reservoir size; and other like considerations and can arrange the system to perform such functions as: dosage control; frequency of medication; variation of medication scheduling and dosage; various warnings and conditions, such as a low battery, error in programming the electronic controls, pressing of keys 134, and an empty reservoir; residential reservoir medication amount; and other like functions for particular medications, particular patients, particular needs, etc.

Casing 50 further includes an L-shaped casing portion 136 extending from sidewall 57 and between sidewalls 56 and 58. Specifically, portion 136 includes a first leg 138 having a first end integrally connected to sidewall 57 and having a second end integrally connected to a second leg 140. The free end of leg 140 extends into open bottom 54 of casing 50.

In its most preferred form, flat portion 66 of chassis 64 has a shape and size complementary to and for receipt in open bottom 54 of casing 50. Control module 12 further includes sealing members 142 located between the ends and sides of portion 66 of chassis 64 and sidewalls 56–69 of casing 50. Further, sealing member 144 is located between the free end of leg 140 of L-shaped casing portion 136 and the top surface of flat portion 66 of chassis 64.

It can now be appreciated that with chassis 64 located in casing 50 with flat portion 66 located within open bottom 54, a substantially water tight compartment which includes motor 118, the electronic controls, the pumping mechanism 62, and other system components is defined by sidewalls 56–59, top 52, and L-shaped casing portion 136 of casing 50, flat portion 66 of chassis 64, expulsor 86, valves 100 and 102, gasket 90, and sealing members 142 and 144. Thus, the system components within this water tight compartment are protected from dust, the elements, or other contaminants which may produce damage thereto.

System 10 in the preferred embodiment includes provisions 146 for removably holding the reservoir module 14 to the control module 12 and is shown in its most preferred form as a locking mechanism. Locking mechanism 146 generally includes, in the preferred embodiment, a latch guide 148, a latch button 150, a locking bolt 152, a pin 154, and a spring 156. Latch guide 148 generally includes a flat portion 158 which is captured between the halves of casing 50. A cylindrical member 160 is further provided depending from the end of flat portion 158 for rotatably and slideably receiving latch button 150. Ears 162 are provided on cylindrical member 160 for capturing between the halves of casing 50. A longitudinally extending, arcuate portion 164 is further provided on latch guide 148 depending from flat portion 158 and having a first end secured to cylindrical member 160. The second, free end of arcuate portion 164 includes a helical, camming portion 166 having stops 168 and 170 formed in and by arcuate portion 164. Camming portion, 166 further includes a detent 172 formed adjacent stop 170 at the longitudinally inward end of camming portion 166.

Latch button 150 generally includes a shank portion 174 which is rotatably and slideably received in cylindrical member 160 of latch guide 148 about its longitudinal axis and a head portion 176 which prevents shank portion 174 from passing through cylindrical member 160 in a first direction. Latch button 150 further includes an eccentric portion 178 which is eccentrically located with respect to the longitudinal axis of shank portion 174 and an extended shank portion 180.

Locking bolt 152 generally includes a cylindrical portion 182 having a shape and size complementary to and for receipt on eccentric portion 176 of latch button 150. Locking bolt 152 further generally includes a T-shaped member 184 extending from cylindrical portion 182. T-shaped member 184 generally includes a leg member 185 having its first end connected to cylindrical portion 182 and its second end connected substantially to the middle of a cross member 186. Cross member 186 includes a first inner end 187 and a second, outer end 188. Cross member 186 includes a surface 189 located on the upper surface of cross member 186 between leg member 185 and end 187 for engaging with central portion 39 of U-shaped member 36 of pressure plate 20.

Locking bolt 152 is held on eccentric portion 178 of latch button 150 in the preferred embodiment of the present invention between a shoulder formed between shank portion 174 and eccentric portion 178 and pin 154 extending through the extended shank portion 180 of latch button 150. Pin 154 further acts as the follower for camming portion 166 and for detent 172 of arcuate portion 164 of latch guide 148. Pin 154 also prevents shank portions 174 and 180 and eccentric portion 178 from passing through cylindrical member 160 in the opposite direction of head portion 176. In its most preferred form, when latch button 150 is located at its first, extreme outward, unlocked position, pin 154 abuts with camming portion 166 adjacent stop 168 and end 188 of T-shaped member 184 of locking bolt 152 abuts with cylindrical member 160 of latch guide 148. Pin 154 further acts as an abutment for spring 158, with the spring 158 located concentrically on latch button 150 and extending between leg 140 of L-shaped casing portion 136 and pin 154. Thus, spring 158 biases latch button 150 in an outward direction.

Locking mechanism 146 further includes provisions 190 for allowing the longitudinal movement of locking bolt 152 but preventing rotatable movement of locking bolt 152 with latch button 150. Provisions 190 are shown in the preferred embodiment of the present invention as tracks formed in the top surface of flat portion 66 of chassis 64 intermediate aperture 130 and its second end and having a shape complementary to and for slideable receipt of cross member 186 of T-shaped member 184 of locking bolt 152.

Suitable provisions 191 for rotating latch button 150 may further be provided for locking mechanism 146. In a first preferred form, provisions 191 include a cavity 192 formed in head portion 176 of latch button 150 having a concentrically located, upstanding post 193. In the preferred embodiment, cavity 192 has a multisided perimeter, such as a hexagonal cross section and post 193 has a shape such as a circular cross section. Provisions 191 further includes a key 194 having a lug end 196 having a shape complementary to and for receipt within cavity 192, with the end 196 having a cavity 198 located generally concentrically therein. Cavity 198 has a size and shape complementary to and for receipt on post 193. It can then be appreciated that locking mechanism 146 utilizing key 194 restricts the personnel who can unlock reservoir module 14 from control module 12. Specifically, keys 194 would be given only to physicians, pharmacists, and other authorized persons and not be given to patients utilizing system 10 or other unauthorized persons. Thus, without keys 194, the patients would be unable to rotate latch button 150 and release locking mechanism 146.

If restricted access is not required, provisions 191 may include an arcuate cavity formed in head portion 176 of latch button 150 for receiving the edge of a coin or similar object. Thus, by turning the coin, latch button 150 may be rotated. However, provisions 191 may take other forms according to the present invention.

The operation of locking mechanism 146 can now be set forth and appreciated. For the sake of example, it will be assumed that U-shaped member 136 of pressure plate 20 is extending through aperture 130 of flat portion 66 of chassis 64 and latch button 150 is in its outward, unlocked position. To lock locking mechanism 146, latch button 150 may be pressed from its first position inwardly within latch guide 148 against the bias of spring 156 towards its second position. When latch button 150 is moved inwardly, locking bolt 152 secured thereto by pin 154 also moves inwardly, with surface 189 of cross member 186 of locking bolt 152 being located under the central portion 39 of U-shaped member 36 of pressure plate 20. At that time, latch button 150 may be rotated to its third position utilizing provisions 191. Due to the eccentric interaction between locking bolt 152 and latch button 150, rotation of latch button 150 causes locking bolt 152 to raise up engaging surface 189 with central portion 39. It should be noted that tracks 190 of chassis 64 prevent locking bolt 152 from rotating with latch button 150. Latch button 150 may be rotated until pin 154 abuts with stop 170 and is located within detent 172 of camming portion 166. At that time, due to its eccentric interaction, locking bolt 152 exerts an upward, locking force on central portion 39 of pressure plate 20. To enhance this exertion of an upward force, surface 189 and central portion 39 may include complementary, wedge-like tapers as in the most preferred form of the present invention. Further, with pin 154 located in detent 172, latch button 150 is prevented from accidentally rotating from its third, inward, locked position.

It should then be noted that if latch button 150 is not located in its third position such that pin 154 is not located in detent 172, pin 154 under the bias of spring 156 will ride back upon camming portion 166 until stop 168. Thus, latch button 150 to which pin 154 is secured rotates and slides back to its first, unlocked position such that locking bolt 152 does not engage with U-shaped member 36. Thus, reservoir module 14 is not secured to control module 12. The reason for this subtle feature is to insure that partial engagement of locking bolt 152 with U-shaped member 36 does not occur. The full engagement of locking bolt 152 with U-shaped member 136 in cooperation with the removable hinge member including hooked portions 34 and hinge pins 128 and standoffs doffs 40–43 insures the proper interrelation between control module 12 and reservoir module 14 for efficient and advantageous operation of pumping mechanism 62 as will be set forth hereinafter.

To unlock locking mechanism 146 releasing locking bolt 152 from U-shaped member 36 of pressure plate 20 and thus allowing removal of reservoir module 14 from control module 12, the locking operation as set forth hereinbefore may be simply reversed.

The removable securement of reservoir module 14 to control module 12 can now be set forth and appreciated. For the sake of example, it will be assumed that reservoir module 14 is removed from control module 12, that bag 18 of reservoir module 14 is full of medicament, and that it is desired to secure reservoir module 14 to control module 12. Specifically, reservoir module 14 may be positioned in a first position with respect to control module 12 such that hooked portions 34 of pressure plate 20 engage with hinge pins 128 of chassis 64 of control module 12. Thus, in the first position, the reservoir module 14 is separable from the control module 12. Reservoir and control modules 12 and 14 may then be moved towards their second position such that hooked portions 34 of pressure plate 20 hook on hinge pins 128 of chassis 64 of control module 12. At that time, control module 12 and reservoir module 14 may be placed on a flat surface such that bottom 24 of casing 16 of reservoir module 14 rests upon the flat surface. Control module 12 may then be pressed firmly in its second position such that U-shaped member 136 of pressure plate 20 of reservoir module 14 extends through aperture 130 of chassis 64 of control module 12. Locking mechanism 146 may then be locked by sliding and rotating latch button 150 in a manner set forth hereinbefore such that locking bolt 152 engages with and raises up central portion 39 of pressure plate 20. When pin 154 is located within detent 172 of camming portion 166, reservoir module 14 is firmly locked in its second position on control module 12. Specifically, reservoir module 14 is removably secured to control module 12 by a removable hinge member including hooked portions 34 and hinge pins 128 at one end and by locking mechanism 146 at its other end. Tube 22 extends between casing 16 of reservoir module 14 and casing 50 of control module 12 through removed portion 48 formed in pressure plate 20 and casing 16.

To remove reservoir module 14 from control module 12, for example to allow replacement of a reservoir module 14 having an empty bag 18 with a reservoir module 14 having a full bag 18, the reservoir module 14 securement procedure as set forth hereinbefore may be simply reversed.

It can then be appreciated that accidental and purposeful separation of control and reservoir modules 12 and 14 is substantially prevented without unlocking locking meachanism 146. Locked in its second position, breakage of hooked portions 34, hinge pins 128, locking bolt 152, and/or U-shaped member 36 must occur before separation of reservoir module 14 from control module 12 can occur without unlocking locking mechanism 146. Accidental dropping of system 10 generally will not cause such breakage. Further, if purposeful breaking force is applied to system 10, breakage of one or more of these components provides evidence of unauthorized separation. Thus, system 10 restricts access of the drug located in bag 18 of reservoir module 14 to authorized personnel. It can then be appreciated that system 10 includes provisions for the removable securement of its modular components which are of simple design and which are easy and inexpensive to manufacture and to assemble.

The operation and subtle features of pumping mechanism 62 and other subtle features of system 10 can now be set forth and appreciated. In its most preferred embodiment, each cycle of the pumping mechanism 62 includes the following valve and expulsor positions. Specifically, in the at rest, stopped, or beginning of the pump cycle, valves 100 and 102 both are in their lowermost position depressing tube 22 and expulsor 86 is at its uppermost position and thus not depressing tube 22. This particular initial position has found to be particularly advantageous since valves 100 and 102 prevent flow through tube 22 in either direction. Further, the position of expulsor 86 beginning at this uppermost position reduces tube 22 deformation since tube 22 is not depressed by the relatively large area of expulsor 86 in the rest position. Further, the position of valve 100 beginning the initiation of its upward movement reduces the starting load on pumping mechanism 62 and thus reduces the size requirement 62 on motor 118 and the energy requirements for motor 118.

Upon rotation of camshaft 74, expulsor 86 compresses tube 22 placing pressure on the medicament in tube 22 between valves 100 and 102. After a slight amount of pressure is placed on tube 22 by expulsor 86, valve 100 moves to its upper position allowing flow of medicament from tube 22 past valve 100. It can then be appreciated that placement of pressure on tube 22 before valve 100 opens substantially prevents back flow of liquid from tube 22 towards valve 102. Back flow of liquid from tube 22 towards valve 102 may cause blood to back up in the catheter of the patient to which tube 22 is connected.

Upon continued rotation of shaft 74, expulsor 86 continues its downward movement. Upon further rotation, expulsor 86 reaches its lowermost position and dwells in its lowermost position while valve 100 returns to its closed, lowermost position. This dwelling of expulsor 86 in its lowermost position also prevents back flow of medicament through tube 22 past valve 100. Upon continued rotation of shaft 74, expulsor 86 starts in its upward movement. Just prior to expulsor 86 reaching its upper position, valve 102 starts in its upward movment. When expulsor 86 reaches its uppermost position, valve 102 also reaches its uppermost position. When camshaft 74 is continued in its rotation, valve 102 moves downward, while expulsor 86 dwells in its uppermost position. Upon continued rotation of camshaft 74, valve 102 returns to its closed, lowermost position, expulsor 86 dwells at its uppermost position, valve 100 dwells at its lowermost position, and indicator 84 activates an optical switch causing the driving of shaft 74 by motor 118 to be stopped at the rest pump cycle.

It can then be appreciated that with reservoir module 14 secured to control module 12, at least one of the valves 100 and 102 engages with and compresses tube 22 against flat portion 32 of plate 20 at all times. Thus, accidental infusion of fluid through tube 22 such as under the influence of gravity or by compression of bag 18 is prevented.

It may also be appreciated that pumping mechanism 62 may rely on the recovery of tube 22 for maintaining contact of expulsor 86 and valves 100 and 102 with cam portions 76, 78, and 80, respectively, during the pumping cycle. However, as in the preferred embodiment, gasket 90 or other biasing members may be utilized to assist expulsor and valve contact with cam portions 76, 78, and 80.

It can be further appreciated that the spacing between flat portion 32 of pressure plate 20 and flat portion 66 of chassis 64 has been found, thusfar, to be very important in maximizing the efficiency and advantageous operation of pumping mechanism 62. Specifically, it has been found that the travel distance of expulsor 86 and valves 100 and 102 through apertures 88, 104, and 106 of flat portion 66 is a constant system characteristic. Thus, if the spacing between pressure plate 20 and chassis 64 varies, disadvantageous operation of pumping mechanism 62 occurs. Specifically, if the spacing is too great, expulsor 86 and/or valves 100 and 102 may not compress tube 22 sufficiently or may not compress tube 22 at all. If insufficient compression of tube 22 occurs, valves 100 and 102 may not prevent flow through of medicament through tube 22 in their lowermost, closed positions. Likewise, expulsor 86 may not have sufficient stroke to compress tube 22 for forcing the desired amount of the medicament out of tube 22 past valve 100, thus greatly reducing efficiency and degrading the accuracy of system 10.

On the other hand, if the spacing between chassis 64 and pressure plate 20 is too small, material from which tube 22 is formed may deform. Such deformation is undesireable for several reasons. First, tube 22 may not fully recover after compression to its uncompressed condition. This is very undesireable because this degrades the accuracy of system 10. Specifically, the volume of medicament pumped by system 10 is directly related to the volume of the tube being compressed by expulsor 86. If plastic deformation occurs to tube 22 due to overcompression by expulsor 86 and valves 100 and 102 of pumping mechanism 62, the volume compressed by expulsor 86 may change and thus change the volume of medicament being pumped by system 10. Since the delivery of medicament at prescribed rates is critical in many medical treatments, such changes in pumping volume is very disadvantageous. Additionally, such deformation may lead to the cracking and/or rupturing of tube 22. Further, if the spacing between chassis 64 and pressure plate 20 is too small, greater force is required to compress tube 22 which is detrimental in the short run by excessive use of energy and in the long run by increased wear on the pumping mechanism 62.

It can then be appreciated that in its most preferred form, plate 20 is separable from chassis 64 due to their inclusion in separate modules 12 and 14. Thus, maintenance of the desired spacing between plate 20 and chassis 64 cannot be factory set but must be insured between control module 12 and a variety of reservoir modules 14 each having different tolerances. To insure proper space maintenance while eliminating the requirement for individual adjustment, standoffs 40–43 are provided. In their most preferred form, standoffs 42 and 42 have a height generally equal to the desired spacing between plate 20 and chassis 64 and standoffs 40 and 43 have a height slightly less than the desired spacing between plate 20 and chassis 64. It can then be appreciated that due to the placement of hinge pins 128 and hooked portions 34 and the upward force exerted on the opposite end of pressure plate 20 by the engagement of the locking mechanism 146, pressure plate 20 is drawn against chassis 64 to insure that the spacing between chassis 64 and the pressure plate 20 is not too great. Further, with chassis 64 drawn towards pressure plate 20, standoffs 41 and 42 abut with chassis 64 to insure that the spacing between chassis 64 and pressure plate 20 is not too small. Thus, standoffs 41 and 42 prevent pressure plate 20 and tube 22 mounted thereon from moving closer to chassis 64. Therefore, standoffs 41 and 42 insure the desired spacing is maintained. In their most preferred form, standoffs 40 and 43 are spaced from chassis 64 when reservoir module 14 is secured to control module 12. However, if the tolerances of any particular reservoir module 14 is greatly different than the norm, standoffs 40 and 43 act as safeguards to prevent pressure plate 20 and tube 22 mounted thereon from moving closer to chassis 64 at their respective locations when they abut therewith. Therefore, according to the present invention, the desired spacing of pressure plate 20 and tube 22 mounted thereon is insured to maximize system efficiency and its advantageous operation.

It should also be appreciated that standoffs 40–43 also insure that tube 22 is positioned on plate 20 for allowing engagement of expulsor 86 and valves 100 and 102 therewith. Further, tube 22 is held between and is prevented from moving between the first and second portions of standoffs 40–43 due to the abutment of standoffs 41 and 42 and the limited spacing of standoffs 40 and 43 from chassis 64. Thus, when reservoir module 14 is secured to control module 12, engagement of expulsor 86 and valves 100 and 102 with tube 22 is insured and tube 22 cannot move from between standoffs 40–43 during valve and expulsor engagement to insure complete contact of valves 100 and 102 and expulsor 86 with tube 22 at all times.

The specific pumping mechanism 62 shown in synergistic relation to the present invention has a number of advantages over a rotary peristaltic or roller pump. Specifically, roller pumps strip the tubing causing the tubing to advance in the direction of rotation. This necessitates anchoring the tubing near the inlet to the roller pump head. Pumping mechanism 62 compresses tube 22 without pulling it so such anchoring is not required. Additionally, roller pumps require the tubing to be fully occluded. This complete occlusion stresses the tubing and distorts it such that the tubing does not fully recover. The expulsor 86 of pumping mechanism 62 shown need not fully occlude tube 22 and thus stresses in tube 22 may be limited to a level that does not yield unacceptable distortion. Further, threading of the tubing for engagement with the roller head is complicated in roller pumps. Positioning of tube 22 to engage with pumping mechanism 62 can be accomplished in a simple, uncomplicated manner. Likewise, less force is required to partially occlude tube 22 in system 10 of the present invention than required to occlude tubing in a roller pump, which reduction of force being reflected to camshaft 74 resulting in a lower drive torque in the present invention.

Further, the use of active valves 100 and 102 for tube 22 of the present invention are believed advantageous over the use of passive check valves. Passive check valves are prone to allowing undesireable flow therethrough whereas valves 100 and 102 prevent flow through. It should be noted that if undesired flow occurs from the drug container to the patient, the rate of infusion is then not controlled and precise delivery of the drug is not obtained. Further, excessive amounts of drug may be delivered to the patient. Additionally, it should also be noted that undesired flow from the patient towards the drug container may cause blood to back up the catheter of the patient, which is medically undesireable. Specifically, check valves will allow flow through by their nature in one direction whereas valves 100 and 102 of the present invention prevent flow through tube 22 in either direction. Thus, if the reservoir bag was compressed, check valves would open and allow flow through towards the patient whereas valves 100 and 102 of the present invention will not allow such flow through. Likewise, to reduce susceptibility to leakage, check valves have a high crack force which increases the pressure necessary for the pumping action. Valves 100 and 102 are independently driven so that there is no dependence of pressure generated by expulsor 86 such that reduced pumping pressure may be utilized in the present invention. Additionally, check valves are unreliable in seating thus also allowing flow through whereas valves 100 and 102 are reliable in occluding tube 22 for preventing such flow through. Thus, active valves 100 and 102 are clearly advantageous over passive check valves.

In its most preferred form, system 10 may be removably secured to the patient such as by a belt thus allowing the patient to be ambulatory while having a drug continuously administered. Thus, the patient need not be bedridden or have his freedom of movement otherwise restricted but may lead a relatively normal life. Further, system 10 allows certain intravenous therapies to be given without frequent medical attention such as in a hospital environment but in an outpatient basis. Thus, health care costs may be significantly reduced.

It can also be appreciated that the fact that system 10, as disclosed, includes a modular construction featuring a removable reservoir module 14 is particularly advantageous. Specifically, module 14 may be disposable such that resterilization is not required therefor, and mistakes as to mixing of different medicaments in bag 18 and like mistakes are removed. Additionally, reservoir module 14 provides increased protection against tampering of medicaments in bag 18 included within module 14. Further, tube 22 with which pumping mechanism 62 engages is a component of and is replaced with each reservoir module 14. Thus, tube 22 which is most subject to wear and deformation is replaced with each refill greatly reducing the risk of equipment failure. Additionally, the electronic controls, pumping mechanism 62, and other components included in control module 12 remain in a sealed compartment separate from reservoir module 14 and thus are not prone to accidental contact and damage when it becomes necessary to refill or replace bag 18. Further, no adjustments are required to insure proper and efficient operation of pumping mechanism 62 of the present invention when it is secured to any particular reservoir module 14. Specifically, system 10 of the present invention and particularly standoffs 40-43, the hinge connection including hooked portions 34 and hinge pins 128, and locking mechanism 146, automatically insures the proper interrelation between control module 12 and all reservoir modules 14 utilized for efficient and advantageous operation of pumping mechanism 62. Thus, it can be appreciated that the modular construction of system 10 of the present invention is more user friendly than other prior drug delivery systems.

Now that the basic teachings of the present invention have been explained, many extensions and variations will be obvious to one having ordinary skill in the art. For example, it can be appreciated that reservoir module 14 can be formed of casing 16 having different heights to accomodate various sizes of bags 18. Likewise, it can be appreciated that pressure plate 20 can be adapted to support an external bag 18 which is not located in a generally closed casing 16.

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalency of the claims are intended to be embraced therein.

What is claimed is:

1. Modular system for delivering a drug to a patient comprising, in combination: a reservoir module, with the reservoir module comprising, in combination: a container for storing a drug to be delivered by the system, a tube for providing communication between the drug storage container and the patient, and a pressure plate, with the communication providing tube being located and supported on the pressure plate; a control module, with the control module comprising, in combination: a chassis including a first aperture and second and third apertures located on opposite sides of the first aperture; a camshaft rotatably mounted to the chassis having a first cam portion and second and third cam portions located on opposite sides of the first cam portion; an expulsor reciprocably mounted in the first aperture of the chassis for engagement with the first cam portion and for interaction with the communication providing tube; first and second valves reciprocably mounted in the second and third apertures of the chassis for engagement with the second and third cam portions and for interaction with the communication providing tube, and means for rotating the camshaft for reciprocating the expulsor and valves in the apertures of the chassis; means for removably securing the pressure plate of the reservoir module to the chassis of the control module, with the expulsor and the valves of the control module interacting with the communication providing tube on the pressure plate of the reservoir module when the reservoir module is removably secured to the control module for forcing the drug stored in the drug storage container through the communication providing tube at desired rates to the patient.

2. The drug delivery system of claim 1 wherein the removably securing means comprises, in combination: means for removably attaching the pressure plate of the reservoir module to the chassis of the control module along one end, with the removably attaching means having a first position wherein the reservoir module and the control module are separable from each other and a second position wherein the reservoir module and the control module are interconnected and nonseparable from each other; and means for holding the reservoir module, and the control module in their second position.

3. The drug delivery system of claim 2 wherein the holding means comprises, in combination: a lock mechanism.

4. The drug delivery system of claim 3 wherein the removably attaching means comprises, in combination: hinge means, with the hinge means comprising, in combination: hinge pins located on one of the pressure plate of the reservoir module and the chassis of the control module; and hooked portions complementary to and for receipt on the hinge pins located on the other of the pressure plate of the reservoir module and the chassis of the control module.

5. The drug delivery system of claim 1 wherein the reservoir module further comprises, in combination: means for insuring proper spacing maintenance between the pressure plate of the reservoir module and the chassis of the control module for the efficient and advantageous interaction of the expulsor and the valves of the control module with the communication providing tube of the reservoir module.

6. The drug delivery system of claim 5 wherein the spacing maintenance insuring means comprises, in combination: at least first and second standoffs formed on the pressure plate for abutting with the chassis of the control module when the reservoir module and the control module are in their second position, with the first standoff abutting with the chassis of the control module between the first and second apertures and the second standoff abutting with the chassis of the control module between the first and third apertures.

7. The drug delivery system of claim 1 wherein the control module further includes a casing, with the casing having a generally open bottom, with the chassis having a size and shape complementary to and for receipt in the generally open bottom of the casing of the control module; and wherein the drug delivery system further comprises, in combination: means for sealing between the casing and the chassis; and means for sealing between the apertures of the chassis and the expulsor and the valves wherein a substantially water tight compartment is formed and defined by the casing and the chassis of the control module.

8. The drug delivery system of claim 1 wherein the means for sealing between the apertures of the chassis and the expulsor and the valves comprises, in combination: a closed cell foam gasket having apertures corresponding to the first, second, and third apertures of the chassis and for the reciprocal receipt of the expulsor and the first and second valves, with the expulsor and the first and second valves having head portions for abutting with the gasket located on the chassis of the control module.

9. The drug delivery system of claim 8 wherein the gasket has sufficient resiliency to bias the expulsor and the first and second valves against the cam portions.

10. Modular system for delivering a drug to a patient comprising, in combination: a control module; a reservoir module; means for removably securing the reservoir module to the control module; with the reservoir module comprising, in combination: a container for storing a drug to be delivered by the system, and means for providing communication between the drug storage container and the patient; with the control module comprising, in combination: means for forcing the drug stored in the drug storage container through the communication providing means at desired rates to the patient, with the drug forcing means of the control module interacting with the communication providing means of the reservoir module when the reservoir module is removably secured to the control module for purposes of delivering a drug stored in the drug storage container to the patient at desired rates.

11. The drug delivery system of claim 10 wherein the removably securing means comprises, in combination: means for removably attaching the reservoir module to the control module along one end, with the removably attaching means having a first position wherein the reservoir module and the control module are separable from each other and a second position wherein the reservoir module and the control module are interconnected and nonseparable from each other; and means for holding the reservoir module and the control module in their second position.

12. The drug delivery system of claim 11 wherein the holding means comprises, in combination: a lock mechanism.

13. The drug delivery system of claim 12 wherein the removably attaching means comprises, in combination: hinge means, with the hinge means comprising, in combination: hinge pins located on one of the reservoir module and the control module; and hooked portions complementary to and for receipt on the hinge pins located on the other of the reservoir module and the control module 14. The drug delivery system of claim 13 wherein the reservoir module includes a pressure plate, with the communication providing means being located and supported on the pressure plate, with the drug forcing means of the control module interacting with the communication providing means on the pressure plate, with the pressure plate including the hooked portions of the hinge means.

15. The drug delivery system of claim 14 wherein the reservoir module further comprises, in combination: means for insuring proper spacing maintenance between the pressure plate and the control module for the efficient and advantageous interaction of the drug forcing means of the control module with the communication providing means.

16. The drug delivery system of claim 15 wherein the spacing maintenance insuring means comprises, in combination: at least a first standoff formed on the pressure plate for abutting with the control module when the reservoir module and the control module are in their second position.

17. The drug delivery system of claim 16 wherein the drug forcing means comprises, in combination: a camshaft having a first cam portion and second and third cam portions located on opposite sides of the first cam portion; an expulsor reciprocably mounted in the control module for engagement with the first cam portion and for interaction with the communication providing means; first and second valves reciprocably mounted in the control module for engagement with the second and third cam portions and for interaction with the communication providing means; and means for rotating the camshaft for reciprocating the expulsor and valves in the control module.

18. The drug delivery system of claim 17 wherein the drug forcing means further comprises, in combination: a chassis; with the chassis including a first aperture for reciprocably receiving the expulsor and second and third apertures located on opposite sides of the first aperture for reciprocably receiving the first and second valves wherein the spacing maintenance insuring means further comprises, in combination: a second standoff; with the first standoff abutting with the chassis of the control module between the first and second apertures and the second standoff abutting with the chassis of the control module between the first and third apertures.

19. The drug delivery system of claim 18 wherein the control module further includes a casing, with the casing having a generally closed top, a generally closed first sidewall, a generally closed second sidewall, a generally closed third sidewall, a generally closed fourth sidewall, and a generally open bottom, with the chassis of the drug forcing means having a size and shape complementary to and for receipt in the generally open bottom of the casing of the control module; and wherein the drug delivery system further comprises, in combination: means for sealing between the sidewalls of the casing and the chassis; and means for sealing between the apertures of the chassis and the lifters wherein a substantially water tight compartment is formed and defined by the sidewalls and the top of the casing and the chassis of the control module.

20. The drug delivery system of claim 19 wherein the communication providing means comprises, in combination: a tube extending from the drug container to the patient.

21. The drug delivery system of claim 20 wherein the standoffs include first and second portions which are spaced apart a distance equal to and for receipt of the tube therebetween to insure the tube is positioned on the pressure plate to insure complete contact of the expulsor and valves of the control module with the tube at all times when the reservoir module and the control module are located in their second position.

* * * * *